United States Patent [19]

Szejtli et al.

[11] 4,228,160

[45] Oct. 14, 1980

[54] INCLUSION COMPLEX OF CYCLODEXTRIN AND INDOMETHACIN AND A PROCESS FOR THE PREPARATION THEREOF, METHOD OF USE AND PHARMACEUTICAL COMPOSITION

[75] Inventors: Jósef Szejtli; Lajos Szente; Agoston Dávid; Sándor Virág; Gyula Sebestyén; Attila Mándi, all of Budapest, Hungary

[73] Assignee: Chinoin Gyógyszer és Vegyészeti Termekék Gyára Rt., Budapest, Hungary

[21] Appl. No.: 6,185

[22] Filed: Jan. 24, 1979

[30] Foreign Application Priority Data

Jan. 27, 1978 [HU] Hungary .............................. CI 1803

[51] Int. Cl.² .................. A61K 31/70; C08B 37/16
[52] U.S. Cl. ...................................... 424/180; 536/103
[58] Field of Search ......................... 424/180; 536/103

[56] References Cited

U.S. PATENT DOCUMENTS

| | | | |
|---|---|---|---|
| 2,959,580 | 11/1960 | Schlenk et al. | 536/103 |
| 3,061,444 | 10/1962 | Rogers et al. | 536/103 |
| 4,054,736 | 10/1977 | Hayashi et al. | 536/103 |

FOREIGN PATENT DOCUMENTS 997638  7/1965  United Kingdom .

OTHER PUBLICATIONS

Frank, Sylvan G., Journal of Pharmaceutical Sciences, Oct. 1975, p. 1585.
Agr. Biol. Chem., vol. 34, No. 12, pp. 1787–1794 (1970).
Hamada et al., Chem. Pharm. Bull., 23, 1205 (1975).
Kurozumi et al., Chem. Pharm. Bull., 23, 3062 (1975).

*Primary Examiner*—Stanley J. Friedman
*Attorney, Agent, or Firm*—Karl F. Ross

[57] ABSTRACT

The invention relates to an inclusion complex of 1-(p-chloro-benzoyl)-5-methoxy-2-methyl-indol-3-yl-acetic acid (indomethacin) and cyclodextrin of a molar ratio of about 2:1. The inclusion complex can be prepared by reacting about 2 moles of alpha or beta cyclodextrin with about 1 mole of 1-(p-chloro-benzoyl)-5-methoxy-2-methyl-indol-3-yl-acetic acid under heating in the presence of an organic solvent which dissolves indomethacin and does not form a stable complex with cyclodextrin. The new complex is at least as active antiinflammatory agent as indomethacin and at the same time shows substantially less ulcerative side-effect.

13 Claims, 5 Drawing Figures

INCLUSION COMPLEX OF CYCLODEXTRIN AND INDOMETHACIN AND A PROCESS FOR THE PREPARATION THEREOF, METHOD OF USE AND PHARMACEUTICAL COMPOSITION

FIELD OF THE INVENTION

The invention relates to new inclusion complexes of cyclodextrin formed with Indomethacin.

BACKGROUND OF THE INVENTION

Cyclodextrins are known to form inclusion complexes with other molecules of suitable size and polarity (J. Pharm. Sci. 64, 1585; 1975). Cyclodextrins (or Schardinger dextrins) are cycloamyloses or cycloglucanes, cyclic oligosaccharides, the most significant representatives of which are α-cyclodextrin consisting of 6 anhydroglucopyranose units and β-cyclodextrin consisting of 7 anhydroglucopyranose units. 1-(p-Chlorobenzoyl)-5-methoxy-2-methyl-indol-3-acetic acid (Indomethacin[R]) is a known antiinflammatory drug, but its disadvantage is its ulcerative effect (British Pat. No. 997.638). This compound shows further a protective effect during pregnancy.

We have now surprisingly found, that the inclusion complex of cyclodextrins with Indomethacin in a molar ratio of about 2:1 is free of the ulcerative side-effect and at the same time it exhibits entirely the same antiinflammatory activity and protective activity during pregnancy as Indomethacin.

The invention also provides a process for the preparation of the inclusion complex of cyclodextrin with indomethacin in a molar ratio of about 2:1 comprising reacting about 2 moles of α- or β-cyclodextrin with 1 mole of 1-(p-chloro-benzoyl)-5-methoxy-2-methyl-indol-3-yl-acetic acid.

The interaction of cyclodextrins and indomethacin was investigated by Hamada, Nambu and Nagai (Chem. Pharm. Bull., 23, 1205; 1975). They observed, that by increasing the concentration of cyclodextrin in an aqueous solution, the solubility of Indomethacin is also increased. The original solubility could be increased from $3.5 \times 10^{-4}$ moles/liter at 35° C. to $9.8 \times 10^{-4}$ moles/liter, i.e. the solubility was increased 2.8 times.

It has been disclosed, that Indomethacin in the presence of glucose hydrolyses rapidly in an aqueous solution, slowly in the presence of α-cyclodextrin and the β-cyclodextrin inhibits hydrolysis.

Kurozumi, Nambu and Nagai (Chem. Pharm. Bull., 23, 3062; 1975) have tried to prepare the cyclodextrin-indomethacin complex. According to one attempt 100 ml. of a solution of $10^{-3}$ molar cyclodextrin was shaken at room temperature with 20 ml. of $3 \times 10^{-3}$ molar ethereal indomethacin solution for 24 hours and the product was crystallized on cooling to 2° C. The precipitated product, however, did not contain any Indomethacin but included pure β-cyclodextrin. This has been explained in the mentioned article by saying that the hollow diameter of β-cyclodextrin is only 7–8 Å, while the diameter of the Indomethacin molecule is 8.5 Å, i.e. it is too large to be incorporated into the hollow of β-cyclodextrin.

There has also been an attempt to prepare the complex by lyophilization. Indomethacin was converted to an ammonium salt with 28% aqueous ammonium hydroxide; it was thus dissolved in water and an equimolar amount of β-cyclodextrin was added in the form of an aqueous solution, the mixture was frozen and lyophilized. The obtained product contained both the starting indomethacin and cyclodextrin in the form of a mixture, i.e. a molar ratio of 1:1 (the molar ratio of Indomethacin: CD=0.92:1, according to the article). The authors referred to X-ray diffraction powder diagrams in order to prove that the 1:1 molar mixture is in fact a complex, but the diagrams have not been disclosed. X-ray diffraction powder diagrams of a complex obtained from ibufenac by crystallization and lyophilization have been disclosed in the article, and it can be seen, that the power diagram of the lyophilized β-cyclodextrin and the powder diagram of the lyophilized ibufenac-β-cyclodextrin complex are substantially identical, corresponding to an amorphous state. It is generally known that amorphous powders obtained by lyophilization do not show significant characteristics by X-ray diffraction powder exposure techniques. Takeo and Kuge (Agric. Biol. Chem., 34, 1787; 1970) report that β-cyclodextrin inclusion complexes in an anhydrous dried state yield identical X-ray diffraction powder diagrams independently of the type of the complex-forming host molecule. The fact of the complex formation cannot be determined by means of X-ray diffraction data in case of lyophilized materials.

Consequently it was not the preparation of an Indomethacin-cyclodextrin complex that was disclosed in the above-mentioned article, but rather a physical mixture of the ammonium salt of Indomethacin and cyclodextrin as the product. According to our observations salts of Indomethacin cannot be incorporated in a cyclodextrin inclusion complex, the salts prove to be too ionic, i.e. hydrophilic.

The above mentioned Japanese authors set as an aim to prepare an 1:1 molar complex, but they did not succeed.

DESCRIPTION OF THE INVENTION

The present invention relates to a complex formed by about two molecules of cyclodextrin and one molecule of Indomethacin.

Figure 1A:
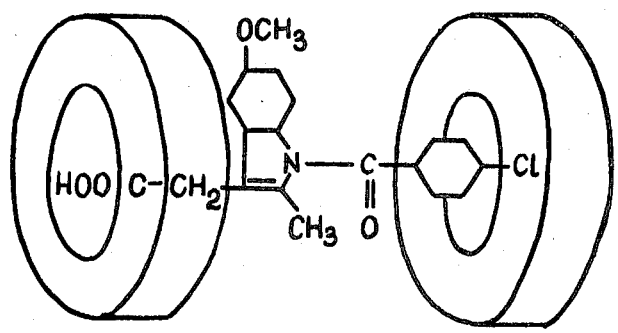
FIG. 1A is a diagram of the cyclodextrin/Indomethacin inclusion complex of the invention.
Figure 1:
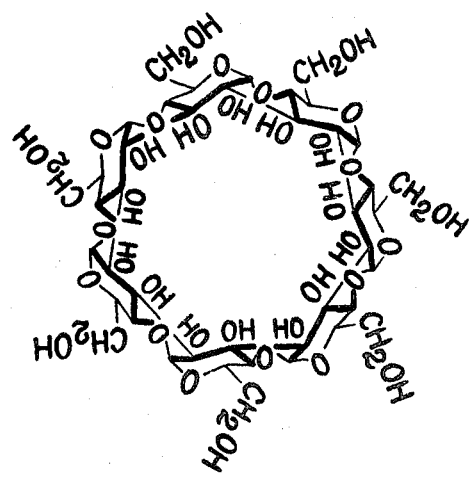
FIG. 1 is a structural formula of cyclodextrin.

Indomethacin can be considered a bifunctional compound from the point of view of cyclodextrin inclusion complex-formation, since part of the Indomethacin molecule (the p-chlorophenyl-group) can be incorporated exclusively in the hollow of one cyclodextrin molecule (the another part of the molecule, the part containing carboxy) is incorporated in another cyclodextrin molecule. The composition of the complex is accordingly shown schematically in FIG. 1A, the hollow discs symbolize cyclodextrin which is to be seen below in FIG. 1.

The molar ratio of cyclodextrin and Indomethacin is 2:1. A complex of a molar ratio 1:1 may also be prepared. The formation of a complex of a molar ratio 1:1 not only does not decrease but increases the detrimental side-effects of Indomethacin, whereas surprisingly the complex of a molar ratio 2:1 considerably reduces adverse side-effects. Physico-chemical data also support the difference between the two complexes; for example the acid dissociation constant value (p$K_a$) considerably increases with two cyclodextrin rings in the complex.

The process of the invention is carried out by reacting the aqueous solution of cyclodextrin with a solution of Indomethacin in an inert solvent. As an inert organic solvent organic solvents are employed which dissolve Indomethacin and do not themselves form a stable complex with cyclodextrin. $C_{1-3}$ alkanols (such as methanol or ethanol), ketones (such as acetone), and ethers (such as tetrahydrofuran or diethylether) are preferred. The reaction is preferably carried out at a temperature of 50° to 100° C., preferably at 60° to 80° C. The reaction can be performed only with heating; in the inner hollow of the cyclodextrin there are water molecules fixed with hydrogen bonds which may be split off only by increasing temperature. The reaction is completed within a few hours. The complex is isolated, preferably by cooling, filtration, or centrifuging of the reaction mixture.

According to another embodiment of the present invention the cyclodextrin is formed from a starch prehydrolized in the reaction mixture by means of cyclodextrinase enzyme. According to the process the starch suspension is gelated at an elevated temperature (100° to 200° C.) and prehydrolyzed partially with alpha amylase. The hydrolysate is sterilized and cyclodextrinase enzyme e.g. starch cyclodextrin-trans-glycolase enzyme is added. The conversion is continued for 2 to 7 days at a temperature of 40° to 50° C. The cyclodextrin-containing mixture thus obtained is heated optionally after dilution with water in order to inactivate the enzyme, and alcohol is added under heating, the obtained slurry is cooled, filtered and a solution of Indomethacin in an organic solvent is added to the filtrate. The inclusion complex forming reaction and the isolation of the product is carried out as described above. The molar ratio of about 2:1 can deviate from 2:1 ratio not more than by ±10%, i.e. the molar ratio can be 2:0.9–1.1 (i.e. 2:0.9 to 2:1.1).

The new cyclodextrin indomethacin inclusion complex thus prepared may be formulated by adding inert solid or liquid carriers and optionally pharmaceutical excipients by methods known per se to give pharmaceutically acceptable pharmaceutical compositions.

The pharmaceutical compositions is preferably formulated in a form suitable for oral administration, for example in the form of tablets, capsules. It must be taken into account during the formulation, that the Indomethacin content of the inclusion complex is about 15 to 20%. One of the components of the inclusion complex, i.e. the cyclodextrin, is a favorable carrier. According to an advantageous embodiment, the mass of the tablet may be supplemented by a further amount of cyclodextrin and thus the equilibrium of the complex formation in a biological medium—in the stomach—is shifted further into the desired direction and thus the probability of the ulcerative effect is further reduced.

If the complex is administered orally, the daily dose is 25 to 200 mg./kg. bodyweight calculated for the Indomethacin content of the inclusion complex and can be administered in one or several portions in the course of the day.

The new complex possesses several considerable physicochemical and pharmaceutical advantages over Indomethacin alone. The complex has the antiinflammatory effect of Indomethacin but considerably less ulcerative wide-effects and thus the complex may be favorably employed as an antiinflammatory agent having pregnancy protective effect with significantly reduced detrimental wide-effects. The complex is much more soluble than Indomethacin. Absorption tests show that Indomethacin administered in the form of a complex ensures a higher blood level than free Indomethacin and the absorption of the Indomethacin from the complex is more efficient than is the case where Indomethacin is administered in a free form.

SPECIFIC EXAMPLES

Further details of the invention are illustrated by the following Examples.

EXAMPLE 1

11.35 g. (0.01 mole) of $\beta$-cyclodextrin are dissolved in 110 ml. of water and to this saturated aqueous solution a solution of 1.78 g. of Indomethacin in 20 ml. of acetone is added (calculated as a ratio 2 moles of $\beta$-cyclodextrin to 1 mole of Indomethacin) under stirring at 70° C. The solutions are combined and the reaction mixture is cooled for 6 hours and 12 hours in a refrigerator. Under cooling white, crystalline precipitate is separated which is filtered, washed with cold acetone or ether and dried over phosphorus pentoxide. The Indomethacin content of the complex is determined by dissolving the crystalline substance in water under mild heating and decomposing with alcohol. The substance is then subjected to photometry at 320 nm. The Indomethacin content of the complex is 14%, molar ratio: $\beta$-cyclodextrin: Indomethacin = 1:0.46.

UV spectra of the Indomethacin set free from the complex and of the original Indomethacin are identical.

The fact of the complex formation is proved by the following observations:

SOLUBILITY TESTS

Both Indomethacin and its cyclodextrin complex of a molar ratio = 2:1 are substantially insoluble at pH = 2. At a pH-value of 4 the solubility of the complex is higher by 33%, at pH = 6 by 112%, at pH = 7 by 223% and at pH = 8 by more than 1000% than that of Indomethacin.

It has been demonstrated by thin layer chromatography that under such circumstances Indomethacin is not decomposed.

A significant difference appears in the IR-spectra of Indomethacin, $\beta$-cyclodextrin and of the inclusion complex of Indomethacin and cyclodextrin of a molar ratio 2:1, as the 1618 cm.$^{-1}$ band characteristic for p-chloroaryl groyp disappears in the case of the complex.

Roentgenograph of X-ray diffraction powder diagram shows that the intensive peak characteristic of cyclodextrin, appearing normally at 2 ⓧ = 10.0° is shifted to 2 ⓧ = 10.5° in the complex. According to article: Chem. Pharm. Bull. 23, 3062 (1975) the roentgen diffraction diagram of cyclodextrin-Indomethacin mixture prepared by lyophilization did not show any significant characteristics.

DIFFUSION TESTS

The two sides of a diffusion cell are separated by a semipermeable membrane. To one half of the cell indomethacin in a buffer of pH = 7, and to the other half a pure buffer is placed.

After 4 hours at room temperature the Indomethacin is distributed between the two cell sides in a ratio of 50:50% and the equilibrium is complete. If the Indomethacin-buffer solution is placed again to one side but the same buffered solution of $\beta$-cyclodextrin is placed to the other side, then there will be more Indomethacin on the $\beta$-cyclodextrin side after 4 hours, than on the Indomethacin side, the cyclodextrin "pumped" over part of the Indomethacin due to complex formation. If a solution of the complex of β-cyclodextrin: Indomethacin=2:1 is placed already at the beginning to one side of the cell and a pure buffer solution on the other side, then more than 70% of the Indomethacin can be found on the starting side after 4 hours and the equilibrium can be achieved only in about more than 10 hours time.

OPTICAL ROTATION DISPERSION TESTS

Cyclodextrin does not show UV absorption, but shows optical rotation, while Indomethacin shows UV absorption, but does not show optical rotation as it does not contain any asymmetric carbon atom. The complex of molar ratio=2:1 has both optical rotation and UV absorption, and thus Cotton-effects induced in the region of the original absorption bands appear.

Circular dichroism spectra prove that even in a $10^{-4}$ molar solution 10 to 20% of the components appear in an associated state, i.e. the complex is rather stable.

THIN LAYER CHROMATOGRAPHY TEST

The chromatography is carried out on a Silicagel G layer; as the developing system a 98:1.5:0.5 mixture of chloroform, ethanol and acetone is employed and the chromatogram is sprayed with 1 g. of p-dimethylaminobenzaldehyde+50 ml. of 36% hydrochloric acid+50 ml. of ethanol and after heating to 50° C. the $R_f$ value of the Indomethacin is 0.92 and the $R_f$ value of the Indomethacin-cyclodextrin complex of molar ratio 1:2 is only 0.10.

DETERMINATION OF $pK_a$ VALUES 0.1 mole/liter potassium chloride and $10^{-3}$ mole/liter Indomethacin and a complex of cyclodextrin and Indomethacin of a 1:1 molar ratio and a complex of cyclodextrin and Indomethacin of a molar ratio of 2:1 were dissolved in a 1:1 mixture of water and ethanol at 25° C. The solutions were titrated with sodium hydroxide by using a glass electrode and the pK values were determined. pK of Indomethancin=5.39, and pK of the 1:1 molar complex=5.43) (substantially the same as pK of Indomethacin), pK of the 2:1 complex is, however 5.54.

This result indirectly proves, that in the complex of molar ratio 1:1 the cyclodextrin ring can be found relatively farther from the carboxy group, i.e. on the p-chlorophenyl group, while in the complex of molar ratio of 2:1 both parts of the Indomethacin molecular are incorporated into a complex; that is why the $pK_a$ value increases, i.e. the acid character is reduced.

The activity of the cyclodextrin and Indomethacin complex of a molar ratio 2:1 and the absence of the ulcer-inhibiting activity of the complex of molar ratio 1:1 is proved in the following biological tests.

The 1:1 complex was prepared as described in Example 1, but 1 mole of cyclodextrin was reacted with 1 mole of Indomethacin. The subacute toxicity of the obtained product was tested in the same way as the toxicity of the 2:1 complex. The test-results are described below.

RESORPTION TEST 72 starved rats were divided into 3 groups. 5 mg. of Indomethacin was administered to the first group and cyclodextrin complex containing 5 mg. of Indomethacin to the second group and the third group (control) was given only water. After a certain time 3—3 animals were decapitated and were bled to death. The serum was separated from the blood and the Indomethacin content was determined by gas chromatography described in (W. G. Perry: J. Chromatogr., 89, 110, 1974; Helleberg E.: J. Chromatogr., 117, 167, 1976).

Figure 2:
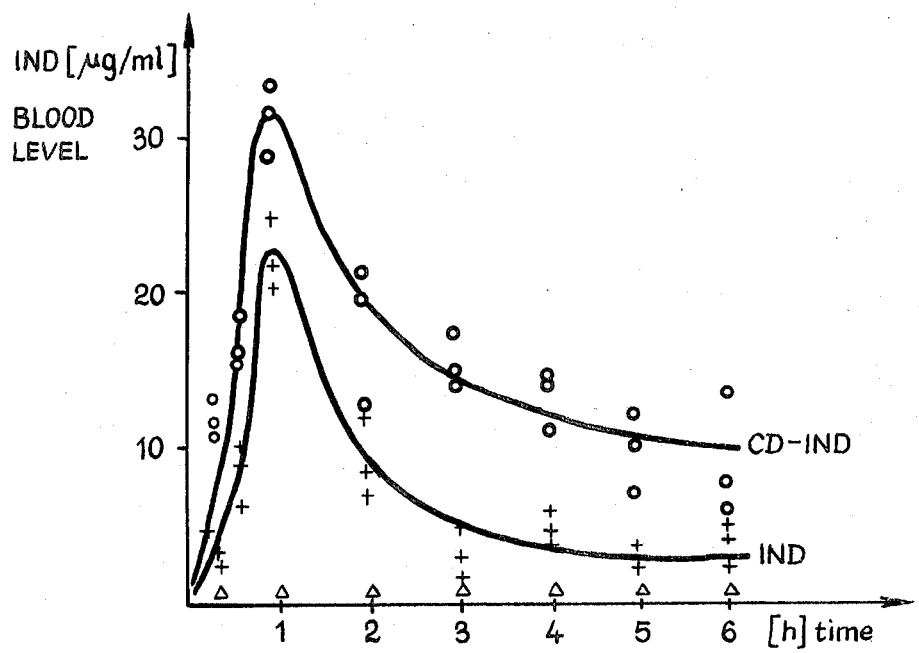
FIGS. 2-5 are graphs showing comparative results with the inclusion complex and Indomethacin alone.

The results are shown in FIG. 2 wherein the blood level in rats induced by Indomethacin or cyclodextrin-Indomethacin of molar ratio 2:1 (the amount of Indomethacin is in both cases 5 mg.) is plotted against the time spent after administration. As seen in FIG. 2 the Indomethacin administered in the form of a complex ensures a higher blood level during the whole time, than free Indomethacin.

---

CD + IND = the complex prepared according to Example 1.
IND = Indomethacin.

---

Test of pregnancy protective activity of Indomethacin and Indomethacin-β-cyclodextrin complex in the ovariectomized rat Test-compound: β-cyclodextrin:Indomethacin complex in a molar ratio of 2:1
Reference substance: Indomethacin (free)
Test animal: female rat of an average weight of 308 g., derived from 18 CFY strain
Treatment:

The ovary of the animals was removed on the 17th day of pregnancy and the animals were placed individually in cages. 6 animals were given per os 1.25 mg./kg. body weight of Indomethacin suspended in water on the 18th day of the pregnancy and 6 animals were given per os a complex containing the same amount of Indomethacin also suspended in water.

6 animals were used as control.

On the 19th day and 20th day in the morning of the pregnancy the treatment was repeated. Thus the animals obtained altogether 6.25 mg./kg. bodyweight of Indomethacin and a complex containing a corresponding amount of Indomethacin.
Results:

The animals were dissected in the morning of the 21st day of pregnancy. The number of the abortions was determined from the number of the implantations of the uterus and the number of the foeti remained in the uterus. Control animals had an average 16.1% of all their foeti were left alive. Two of the six animals had 100% abortion. In animals treated with Indomethacin 58.8% of all the foeti and in the animals treated with the complex 66.7% of all the foeti were left alive. Compared with the control both the treatment with Indomethacin and with the complex significantly increased the percentage of the foetus retention but when comparing Indomethacin with the complex no considerable difference in their activity was shown.

PHARMACOLOGICAL TESTS

Pharmacological test of the antiinflammatory activity

Test-compound: β-Cyclodextrin-Indomethacin complex of molar ratio=2:1.
Reference compound: Indomethacin (free).
Used animals:

The antiinflammatory activity was tested in female rats deriving from the strain CFY, 10—10 animals were used for each substance and each dose.

4–5 weeks old animals of an average weight of 90–110 g. were used at the beginning of the test series. A control group of 10 animals was also used in the series of the test.

Treatment:

The antiinflammatory activity was investigated in an acute test. The animals were given the test compound and the reference Indomethacin per os in the form of a suspension prepared with 1% methyl cellulose through an oesophageal sound.

A dose of 0.1 ml./animal of a 0.5% solution of the inflammation-inducing carragenin was administered subplantar both to the treated and untreated animals.

Doses:

$\beta$-Cyclodextrin-Indomethacin complex was administered in doses: 8.06–16.12–24.18–32.24 and 40.3 mg./kg. and Indomethacin in doses 1-2-3-4- and 5 mg./kg. The $\beta$-cyclodextrin-Indomethacin complex contained 12.4%. 1 mg. of Indomethacin is equivalent to 8.06 mg. of complex and the above doses were administered for the sake of better comparison. The control group was given 1% methyl cellulose per os.

The investigation:

The antiinflammatory activity was carried out in rats starved for 16 hours.

Treatment:

The antiinflammatory substances were administered to the test animals per os, the inflammation inducing carragenin was given subplantar and 1 ml. of lukewarm tapwater was given to each animal per os. 3 hours after the treatment the animals were exterminated and the weight of the separated untreated and carrageenin-treated feet was measured. The separation was carried out above the metacarpus.

Evaluation:

The weight difference of the untreated and treated feet-weight in the same animal was calculated. The weight increase of the control group was considered as 100% and the results of the treated group were compared with the results of the control animals.

Figure 3:
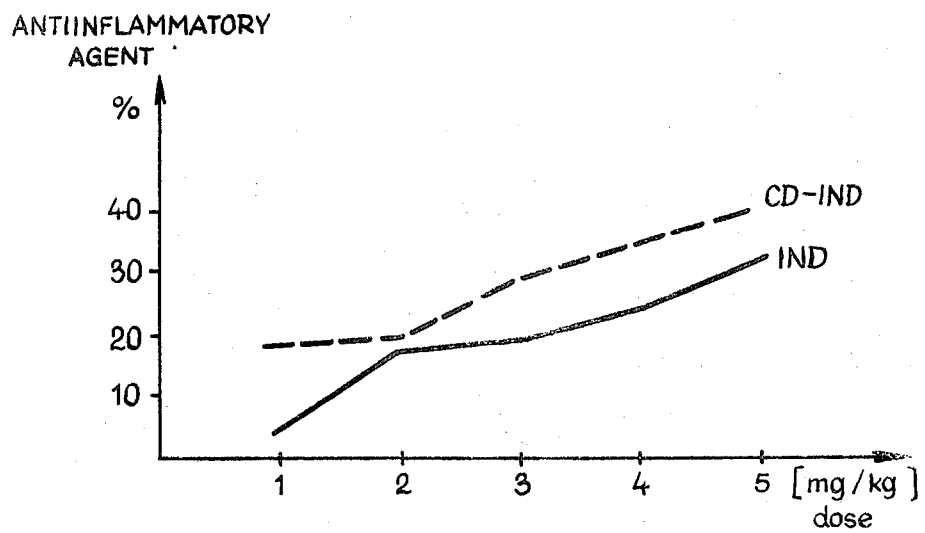

Antiinflammatory activity in the case of the animals treated with different doses of $\beta$-cyclodextrin/Indomethacin complex and Indomethacin was calculated in percent. The obtained results are shown in FIG. 3.

According to our test-results, the activity of $\beta$-cyclodextrin/Indomethacin and Indomethacin compared in acute inflammation, there is no significant difference between the antiinflammatory activities of the two molecules.

The antiinflammatory activity increased in proportion to the degree of increasing the dose and the activity is shifted to the complex. Thus Indomethacin is better absorbed from the complex, than if the Indomethacin is not given in the form of a complex.

Investigation of the speed at which the compound tends to act and the duration of the activity The test compound, the reference substance, the animals, the treatment, doses, investigation are all the same as described above. The differences can be found below.

In this series of tests the following investigations were carried out:
1. Simultaneous administration of the antiinflammatory agent with Carrageenin, evaluation at different times (3, 6, 24 and 28 hours after the treatment).
2. Carrageenin was given 1, 2 and 3 hours after the administration of the antiinflammatory agent and the results were evaluated after 3 hours. The animals were exterminated with ether and the weight of the separated untreated feet and feet treated with Carrageenin was measured. The feet were separated above the metacarpus.

Figure 4:
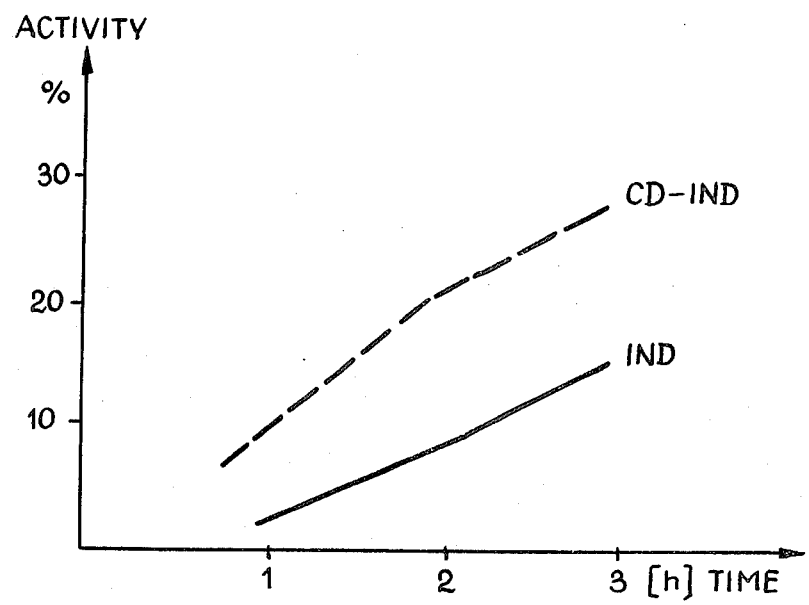

Evaluation:

The weight difference of the untreated and treated feet in the same animal was calculated. The weight increase of the control group was considered as 100% inflammation and the results of the treated groups were compared to this control. The antiinflammatory activity was calculated in percent and the results are plotted in FIGS. 4 and 5.

Figure 5:
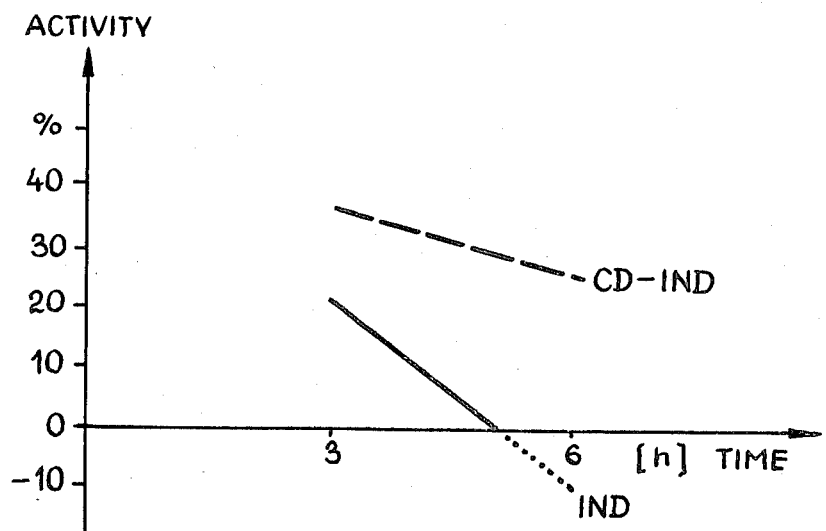

1. When tested, the antiinflammatory agent together with Carrageenin the results showed that the antiinflammatory activity can be still observed and evaluated 3 and, 6 hours after the administration of Carrageenin but after 24 and 48 hours the Carrageenin activity decreases to such an extent that the results cannot be evaluated in a realistic way. According to our test results the $\beta$-cyclodextrin/Indomethacin complex decreased the inflammation more efficiently than the Indomethacin and its activity almost did not decrease 6 hours after the treatment, while in the case of the Indomethacin alone the inflammation increases after 6 hours instead decreases (FIG. 5).

2. 1, 2 and 3 hours after the administration of the antiinflammatory agent Carrageenin and 3 hours later upon evaluation it was found that the antiinflammatory activity of the $\beta$-cyclodextrin/Indomethacin complex is higher than that of Indomethacin alone and the slope of the lines (FIG. 4) shows, that Indomethacin incorporated in the complex acts more rapidly as antiinflammatory agent, than Indomethacin alone.

In can be summarized that the $\beta$-cyclodextrin/Indomethacin complex acts more rapidly and for a longer time than Indomethacin alone.

Subacute toxicity test of $\beta$-cyclodextrin/Indomethacin complex in rat (Ulcer test)

The test-compound is $\beta$-cyclodextrin/Indomethacin complex as prepared according to Example 1 and free Indomethacin is a reference substance.

Animals:

Subacute toxicity test was carried out in male and female animals derived from CFY strain and 10—10 animals were treated for each substance and for male and female rats each.

At the beginning of the investigation the animals were 7 weeks old and weighed 150–170 g. The animals were kept at a constant temperature (22°–24° C.) and under constant relative humidity (45–50%). During treatment the animals were on a standard diet and drank water *ad libitum*.

Treatment:

Subacute toxicity was tested for 4 hours. The animals were treated daily at the same time of the day, in the morning. The test compound and the reference substance were administered in the form of a suspension prepared with 1% methyl cellulose through an oesophagial sound. The animals of the control group obtained 1% methyl cellulose per os. The weight increase of the animals and their clinical states were registered during the treatment every week.

Doses:

1. Control: 1% methyl cellulose suspension 0.2 ml./100 g. per os;

2. 40.3 mg./kg of β-cyclodextrin/Indomethacin p.o. suspension 3. 5.0 mg./kg of free Indomethacin p.o. suspension.

Investigation: the animals were treated for 28 days.

1. Erosion was observed in 10% of the male animals of the group treated with 1% methyl cellulose.

2. 30% of the male animals treated with 40.3 mg./kg. of the complex were dead by the 7th day and 30% of the female animals were dead by the 25th day.

3. 80% of the male animals treated with 5 mg./kg. of Indomethacin were dead by the 14th day and 60% of the female animals were dead by the 21st day.

The number of the ulcers and erosions related to the treated animals in the individual groups is to be found in the following table

|  | ulcus | | erodion | |
|---|---|---|---|---|
|  | male | female | male | female |
| control | 0/10 | 0/10 | 1/10 | 0/10 |
| 40.3 mg./kg. CD-Ind | 2/10 | 1/10 | 4/10 | 4/10 |
| 5.0 mg./kg. Ind. | 7/10 | 6/10 | 9/10 | 7/10 |

The size of the ulcer did not exceed the size of a pin-head.

Bodyweight increase

The bodyweights registered every week are summarized in the following table. The results show that the bodyweight increase of the male and female animals treated with the test compound and the reference compound do not significantly differ from the control. The bodyweight values of female and male animals treated with 5 mg./kg. of Indomethacin give a real picture only until the third week of the treatment due to the large percentage of death.

| | Average bodyweight increase (g.) | | | | |
|---|---|---|---|---|---|
| Male | 0 | 1 | 2 | 3 | 4 (week) |
| control | 152.5 | 196.5 | 240.5 | 276.5 | 300.5 |
| 40.3 mg./kg. Cd-Ind | 161.0 | 206.2 | 253.8 | 303.6 | 339.3 |
| 5.0 mg./kg. Ind | 164.5 | 210.7 | 212.5 | 287.5 | 320.0 |

| Female | | | | | |
|---|---|---|---|---|---|
| control | 154.5 | 183.0 | 209.0 | 222.0 | 241.0 |
| 40.3 mg./kg. Cd-Ind | 164.5 | 190.5 | 212.0 | 212.0 | 228.5 |
| 5.0 mg./kg. Ind | 161.5 | 182.0 | 177.5 | 206.5 | 221.2 |

The following test shows that the formation of a complex of a molar ratio=1:1 does not decrease the detrimental side effects of Indomethacin 16 mg. of the complex of a molar ratio 1:1 prepared as described above are identical with 5 mg. of Indomethacin. As a reference compound pure Indomethacin is used.

Animals:

Subacute toxicity test was carried out in male and female animals derived from Long-Evans strain, 10—10 animals were treated for each test compound and both for female and male animals. At the beginning of the test the animals were 7 week old, of an average bodyweight of 140-160 g. The animals were kept at constant temperature (22°-24° C.) and under constant relative humidity (45-50%). During the treatment the animals were on a standard diet and drank water *ad libitum.*

Treatment:

The subacute toxicity test corresponds to a 4 weeks' treatment period. The animals were treated daily at the same time in the morning. The complex of a molar ratio 1:1 and the reference substance were administered in the form of a suspension in 1% methyl cellulose through an oesophaged sound. The animals of the control group get 1% methyl cellulose per os. The weight increase and the clinical state of the animals were registered during the treatment every week.

Doses:

1. Control: 1% methyl cellulose, 0.2 ml./100 g. per os
2. 1:1 complex 16 mg./kg. per os susp.
3. Indomethacin 5 mg./kg. per os susp.

1 mg. Indomethacin is equivalent to 3.2 mg. of 1:1 complex.

Investigation:

The animals were treated for 28 days. On the $29^{th}$ day the living animals were exterminated with ether and the stomach and the duodenum were prepared. Also the stomach and duodenum of the animals perished during the treatment were prepared.

In each case the mucous membrane of the stomach, bile and intestine were examined macroscopically and the number of the eventual ulcers and erosions was determined.

Test-results:

The death of the treated animals and the number of ulcers found in each group related to the number of the treated animals in each group is given in the Tables below.

| | Lethality | | | | | | | |
|---|---|---|---|---|---|---|---|---|
| | 7th day | | 14th day | | 21st day | | 28th day | |
| | male | female | male | female | male | female | male | female |
| control | 0/10 | 0/10 | 0/10 | 0/10 | 0/10 | 0/10 | 0/10 | 0/10 |
| 1:1 complex 16 mg./kg. | 5/10 | 1/10 | 7/10 | 2/10 | 7/10 | 3/10 | 9/10 | 9/10 |
| Indomethacin 5 mg./kg. | 4/10 | 1/10 | 4/10 | 2/10 | 5/10 | 3/10 | 6/10 | 6/10 |

| | Ulcer and erosion | | | |
|---|---|---|---|---|
| | Erosion | | Ulcer | |
| Group | male | female | male | female |
| Control | 3/10 | 2/10 | 0/10 | 0/10 |
| 1:1 complex 16 mg./kg | 10/10 | 10/10 | 9/10 | 9/10 |
| Indomethacin 5 mg./kg. | 10/10 | 10/10 | 8/10 | 7/10 |

The size of the ulcers did not exceed the size of a pin-head.

Bodyweight increase was registered every week but because of the great lethality of the male and female animals treated with 16 mg./kg. of 1:1 complex and 5 mg/kg. of Indomethacin the evaluation is not realistic.

Clinical symptoms:

Starting on the third day of the treatment symptoms of bradypnoe and depression were observed in animals treated with 5 mg./kg. of Indomethacin and 16 mg./kg. of 1:1 complex. These symptoms were being observed until the death of the animals, until the $28^{th}$ day of the treatment respectively.

Summary:

In 90% of the male and female animals treated with 16 mg./kg. of β-CD Indomethacin complex (1:1 complex) we have found ulcers.

In 80% of the male animals treated with 5 mg./kg. of Indomethacin and in 70% of the female animals we have found ulcers.

According to our test results the detrimental side effect of Indomethacin in case of the 1:1 complex formation increased. The desired ulcer-inhibiting effect is shown only by the 2:1 complex.

EXAMPLE 2

The 30% starch suspension was cooled to 80° C. after gelation at 120° C. and 0.2% by weight of alpha-amylase was added and the mixture was partially prehydrolyzed for 20 minutes. The hydrolyzate was sterilized and 5 units/g. of starch-cyclodextrin.trans-glycosylase-enzyme composition was added under cooling to 50° C., whereafter 5% by Vol. of toluene was added after 4 hours. The conversion was continued for 2 to 7 days and thus the optimal yield of cyclodextrin is achieved. The conversion product is diluted with water to a twofold volume, boiled in order to inactivate the enzyme and 50% by volume of 96% of ethanol is added at 70° C. The slurry thus obtained is cooled to 40° C. and filtered off. The acetone solution of Indomethacin is added to the filtrate taking into account that about 70% of the dry substance is consisting of beta-cyclodextrin. The beta-cyclodextrin Indomethacin complex is crystallized under stirring and slow cooling for 6 hours and after storing for 24 hours at 0° C. The complex is substantially identical with the complex described in Example 1. The difference is, that it contains 5–10% of substances different from β-cyclodextrin related to the dry substance partly alpha-dextrin and partly linear dextrins. These components do not disturb the employability of the product, thus further purification is not necessary, only the possible Indomethacin not incorporated in the complex has to be removed by washing with an organic solvent as described in Example 1. The end product contains 14% of Indomethacin in this case as well.

EXAMPLE 3

Capsules of the following composition are prepared:

| | |
|---|---|
| Inclusion complex according to Example 1 | 166 mg. |
| colloidal silica | 9 mg. |
| talcum | 5 mg. |
| magnesium stearate | 15 mg. |
| potato starch | 20 mg. |
| milk sugar | 20 mg. |
| crystalline cellulose | 40 mg. |
| total weight | 275 mg. |

Capsules are prepared by dry granulation technology known per se.

EXAMPLE 4

Tablets of the following composition are prepared:

| | |
|---|---|
| Inclusion complex according to Example 1 | 330 mg. |
| amylopectine | 10 mg. |
| crystalline cellulose | 60 mg. |
| stearic acid | 12 mg. |
| talcum | 13 mg. |
| total weight | 425 mg. |

Tablets are prepared by dry granulation technique known per se.

What we claim is:

1. An inclusion complex of cyclodextrin and Indomethacin in a molar ratio of about 2:1.
2. An inclusion complex of cyclodextrin and Indomethacin in a molar ratio of 1.9:1 to 2.1:1.
3. A process for the preparation of an inclusion complex in a molar ratio of about 2:1 of cyclodextrin to 1-(p-chloro-benzoyl)-5-methyl-2-methyl-indol-3-yl-acetic acid (Indomethacin) which comprises reacting about 2 moles of α- or β-cyclodextrin with about 1 mole of 1-(p-chloro-benzoyl)-5-methoxy-2-methyl-indol-3-yl-acetic acid with heating to a temperature sufficient to form the inclusion complex in the presence of an inert organic solvent dissolving Indomethacin and not forming a stable complex with cyclodextrin, and isolating the formed complex.
4. A process as defined in claim 3 comprising carrying out the reaction at a temperature of 50° to 100° C.
5. A process as defined in claim 3 wherein a $C_{1-3}$ alkanol, ketone or ether is the inert organic solvent.
6. A process as defined in claim 5 wherein methanol, ethanol, acetone, diethylether or tetrahydrofuran is said inert organic solvent.
7. A process as defined in claim 3 which comprises reacting an aqueous solution of the cyclodextrin with a solution of Indomethacin in said inert organic solvent.
8. A process as defined in claim 3 which comprises adding cyclodextrinase enzyme and a solution of Indomethacin in an organic solvent to an aqueous solution of the prehydrolysed starch.
9. A process as defined in claim 3 which further comprises separating the formed cyclodextrin/Indomethacin complex in a molar ratio of 2:1 by cooling the reaction mixture.
10. The process defined in claim 4 wherein said temperature is 60° to 80° C.
11. A pharmaceutical composition of antiinflammatory activity containing an effective amount of an inclusion complex of cyclodextrin and Indomethacin in a molar ratio of about 2:1 and a pharmaceutically acceptable inert solid or liquid carrier.
12. An antiinflammatory method of treatment comprising administering to an animal subject suffering from an inflammation, a pharmaceutically effective amount of the inclusion complex defined in claim 2.
13. A pregnancy protective method of treatment comprising administering to an animal subject in pregnancy a pharmaceutically effective amount of the inclusion complex defined in claim 2.

* * * * *